(12) United States Patent
Stone et al.

(10) Patent No.: US 11,401,226 B2
(45) Date of Patent: Aug. 2, 2022

(54) SYSTEMS AND METHODS FOR REFINING CANNABIDIOL

(71) Applicant: Mile High Labs, Inc., Broomfield, CO (US)

(72) Inventors: Brad William Stone, Timnath, CO (US); Stephen Culhane Mueller, Loveland, CO (US); Casey James Kikendall, Windsor, CO (US)

(73) Assignee: Mile High Labs, Inc., Broomfield, CO (US)

(*) Notice: Subject to any disclaimer, the term of this patent is extended or adjusted under 35 U.S.C. 154(b) by 71 days.

(21) Appl. No.: 16/875,744

(22) Filed: May 15, 2020

(65) Prior Publication Data

US 2020/0361841 A1 Nov. 19, 2020

Related U.S. Application Data

(60) Provisional application No. 62/849,643, filed on May 17, 2019.

(51) Int. Cl.
| | | |
|---|---|---|
| *C07C 37/00* | (2006.01) | |
| *C07C 37/68* | (2006.01) | |
| *C07C 37/70* | (2006.01) | |
| *C07C 37/72* | (2006.01) | |
| *C07C 37/74* | (2006.01) | |
| *C07C 37/84* | (2006.01) | |
| *C07C 37/86* | (2006.01) | |
| *B01D 11/02* | (2006.01) | |
| *B01D 3/10* | (2006.01) | |

(52) U.S. Cl.
CPC .............. *C07C 37/004* (2013.01); *B01D 3/10* (2013.01); *B01D 11/028* (2013.01); *B01D 11/0288* (2013.01); *B01D 11/0292* (2013.01); *C07C 37/68* (2013.01); *C07C 37/685* (2013.01); *C07C 37/70* (2013.01); *C07C 37/72* (2013.01); *C07C 37/74* (2013.01); *C07C 37/84* (2013.01); *C07C 37/86* (2013.01)

(58) Field of Classification Search
CPC ................................................... C07C 37/004
See application file for complete search history.

(56) References Cited

U.S. PATENT DOCUMENTS

2006/0167283 A1* 7/2006 Flockhart .............. C07C 37/004
549/390
2020/0039908 A1* 2/2020 ElSohly .................. C07C 37/74

* cited by examiner

*Primary Examiner* — Medhanit W Bahta
(74) *Attorney, Agent, or Firm* — Snell & Wilmer L.L.P.

(57) ABSTRACT

A method of making CBD concentrate or CBD Isolate comprises (a) milling a raw material; (b) contacting the milled raw material with an extraction solvent and separating a solid waste material to form a filtered extract; (c) concentrating the filtered extract; (d) washing the concentrated extract to form an organic phase and an aqueous phase; (e) separating the aqueous phase from the organic phase to form a washed extract; (f) removing an organic solvent from the washed extract to form a concentrated washed extract; (g) decarboxylating the concentrated washed extract; (h) vacuum distilling the decarboxylated extract to form a distillate; (i) dewaxing the distillate to form a post-dewax filtrate; (j) applying a vacuum to the post-dewax filtrate to form a post-dewax concentrate; (k) degassing the post-dewax concentrate; and (l) vacuum distilling the degassed concentrate to form a CBD concentrate.

18 Claims, 2 Drawing Sheets

SYSTEMS AND METHODS FOR REFINING CANNABIDIOL

CROSS REFERENCE TO RELATED APPLICATION

This application is based on and derives the benefit of the filing date of U.S. Provisional Application No. 62/849,643 filed on May 17, 2019 entitled "SYSTEMS AND METHODS OF REFINING CANABIDIOL," the contents of which is incorporated herein by reference in its entirety.

BACKGROUND

Cannabidiol (CBD) is one of many cannabinoid species found in various species of cannabis, including hemp and *Cannabis Sativa*. CBD is a non-psychoactive crystalline cannabinoid having a variety of uses. Generally, CBD occurs in plants both as CBD and as cannabidiolic acid (CBDA), which can be extracted and converted to the decarboxylated form (CBD).

Methods for extracting cannabinoids, such as CBDA and CBD from *cannabis* have been described. Some known methods involve extraction with hot gas, liquid $CO_2$, or sub-zero degrees Celsius organic solvent. Some known methods use positive or negative pressure to volatilize cannabinoids, which are then captured by a cold trap.

In addition, some known methods feature at least one or more chromatographic steps, such as passage of a raw extract through one or more columns containing one or more chromatographic media. Some difficulties associated with column chromatography include difficulties in controlling the flow of mobile phase liquids. Columns must be closely monitored during processing to avoid underflow (where the column runs dry) and overflow (where column contents spill and are wasted and/or contaminated). There are also difficulties and costs associated with stationary phase media. Generally, stationary phase media need to be cleaned or regenerated regularly, sometimes even between batches, to work properly. If they cannot be regenerated, they must be discarded.

SUMMARY

Disclosed herein is a method of manufacturing a CBD Isolate, comprising: (a) milling a raw material to produce a milled raw material; (b) contacting the milled raw material with an extraction solvent to form a raw extract and separating a solid waste material from the raw extract to form a filtered extract; (c) concentrating the filtered extract to form a concentrated extract; (d) washing the concentrated extract by dissolving the concentrated extract in an organic solvent to form an organic phase and washing the organic phase with a aqueous phase; (e) separating the aqueous phase from the organic phase to form a washed extract; (f) removing the organic solvent from the washed extract to form a concentrated washed extract; (g) decarboxylating the concentrated washed extract to form a decarboxylated extract; (h) vacuum distilling the decarboxylated extract to form a distillate; (i) dewaxing the distillate to form a post-dewax filtrate; (j) applying a vacuum to the post-dewax filtrate to form a post-dewax concentrate; (k) degassing the post-dewax concentrate to form a degassed concentrate; (l) vacuum distilling the dewaxed concentrate to form a distilled CBD concentrate; and (m) crystallizing CBD from the distilled CBD concentrate to form the CBD Isolate. The raw material may be hemp, cannabis, or marijuana, and may be in various forms, such as pelletized, trimming, buds, or whole plant, or mixtures of two or more of the foregoing. The raw material may comprise CBD and CBDA in various weight ratios. In various embodiments, the raw material is hemp. The raw material may be milled fine. The extraction solvent may comprise a lower alcohol or liquid carbon dioxide. The extraction solvent may comprise a lower alcohol, such as methanol, ethanol, isopropyl alcohol (IPA), or a butanol, such a n-butanol. The extraction solvent may also comprise some water (e.g., as in ethanol-water azeotrope) or alkanes (e.g., butane). In various embodiments, the extraction solvent may be IPA. Finely-milled raw material may be contacted with the extraction solvent in a counter current extractor. Counter current extraction may be carried out in more than one stage, e.g., two stages. The solid waste may be separated from the extraction solvent between extraction stages by centrifugation, e.g., with a scroll centrifuge, and may be further filtered using diatomaceous earth or other filter aid, such as powdered cellulose (e.g., Solka Floc). The method may further comprise recovering at least some extraction solvent from the raw extract and recycling it to a previous step. Concentrating the raw extract to form a concentrated extract may comprise subjecting the raw extract to vacuum distillation. In some embodiments, the organic solvent of step (d) comprises hexanes, heptanes, alkanes, benzene, xylenes, ethyl benzene, or toluene, or mixtures of two or more thereof. The aqueous phase of step (d) may comprise a salt, such as one or more of magnesium sulfate (e.g., an $MgSO_4$ hydrate, such as $MgSO_4.7H_2O$), sodium sulfate, potassium sulfate, lithium sulfate, sodium chloride, potassium chloride, or lithium chloride, or hydrates or combinations of any of the foregoing, as applicable. The aqueous phase may further comprise, or be adjusted to comprise, a lower alcohol, such as isopropyl alcohol, methanol, ethanol, n-butanol, isobutanol, or sec-butanol, or mixtures of two or more thereof. Removing the organic solvent from the washed extract in step (f) may comprise distillation, which may comprise applying heat at a temperature sufficiently high to remove any contaminating water, e.g., about 105° C. The distillation may also comprise recycling at least some of the organic solvent, in which case it is important to separate water from the organic solvent between its being removed from the washed extract and its being recycled to the washing step (d). Decarboxylating the concentrated washed extract of step (g) may comprise applying a vacuum, heat, or agitation to the concentrated washed extract. The vacuum may be less than or equal to about 20 Torr, the heat added may be sufficient to achieve a temperature of 125° C., or agitation (e.g., jet spray) may be applied for at least two hours. Step (g) may also comprise ° an inert gas sweep, such as a nitrogen or argon sweep. The vacuum distillation of step (h) may comprise wiped film distillation or similar short path (molecular) distillation. The dewaxing step (i) may comprise dissolving the distillate in a solvent, adding a filter aid to the solvent, cooling the solvent, filtering, and collecting post-dewax filtrate. The solvent may be acetone, methanol or ethanol, or mixtures of two or more thereof (and may comprise a small amount of water), and the filter aid may comprise diatomaceous earth (DE) or a similar filter aid, such as powdered cellulose (e.g., Solka Floc). The solvent may be recovered, dewatered, and recycled to an earlier step. The degassing of step (k) may comprise applying a vacuum, applying an inert gas sweep, applying heat, and/or agitation. The vacuum may be less than or equal to about 20 Torr, the applied heat may be sufficient for a temperature of about 125° C., the inert gas sweep may be a continuous nitrogen sweep, or the agitation may be applied for at least about one hour. The vacuum distillation of step (l) may comprise wiped film distillation or similar short path (molecular) distillation. Crystallizing the CBD Isolate in step (m) may comprise dissolving the distilled CBD concentrate of step (l) in a crystallization solvent at a first temperature to form a solution, optionally passing the solution through a polish filter; supersaturating the solution (e.g., by slowly lowering the temperature to a second seeding temperature lower than the first temperature, or by removing solvent through evaporation, or both) adding a crystal seed, further saturating the solution (e.g., by lowering the temperature of the seeded solution to a third temperature lower than the first temperature or the second temperature, or by removing solvent through evaporation, or both), and separating crystalized CBD from solvent to form the CBD Isolate. The temperature profile may be optimized to achieve the desired crystal size and purity. The recrystallization solution may be subject to Ostwald ripening, following a program of temperature cycling (cooling and heating), whereby the size of CBD crystals is increased, and any present fines digested away, thereby enhancing the purity, crystal size, filterability, of crystalized CBD. Filtered isolate may be washed with cold solvent, e.g., −20° C. pentane. The method may further comprise packaging the CBD Isolate.

Also disclosed is a CBD Isolate manufactured by the method of the foregoing paragraph.

Also disclosed herein is a method of manufacturing CBD concentrate, comprising: (a) milling a raw material to produce a milled raw material; (b) contacting the milled raw material with an extraction solvent separating a solid waste material from a raw extract; (c) concentrating the raw extract to form a concentrated extract; (d) washing the concentrated extract by dissolving the concentrated extract in organic solvent to form an organic phase and washing the organic phase with a aqueous phase; (e) separating the aqueous phase from the organic phase to form a washed extract; (f) removing organic solvent from the washed extract to form a concentrated washed extract; (g) applying a vacuum to the concentrated washed extract to form a post-decarboxylation extract; (h) vacuum distilling the post-decarboxylation extract to form a distillate; (i) dewaxing the distillate to form a post-dewax filtrate; (j) applying a vacuum to the post-dewax filtrate to form a post-dewax concentrate; (k) degassing the post-dewax concentrate to form a degassed concentrate; (l) vacuum distilling the dewaxed concentrate to form a CBD concentrate. The raw material may be hemp, cannabis, or marijuana, and may be in various forms, such as pelletized, trimming, buds, or whole plant, or mixtures of two or more of the foregoing. In various embodiments, the raw material is hemp. The extraction solvent may comprise a lower alcohol or liquid carbon dioxide. The extraction solvent may comprise a lower alcohol, such as methanol, ethanol, isopropyl alcohol (IPA), or a butanol, such as n-butanol. In various embodiments, the extraction solvent is IPA. In some embodiments, the method may comprise recovering at least some extraction solvent from the raw extract. Concentrating the raw extract to form a concentrated extract may comprise subjecting the raw extract to vacuum distillation. The organic solvent of step (d) may comprises hexanes heptanes, alkanes, benzene, or toluene, or mixtures of two or more thereof. The aqueous phase of step (d) may comprise a salt, such as magnesium sulfate (e.g., an $MgSO_4$ Hydrate, such as $MgSO_4 \cdot 7H_2O$) sodium chloride, potassium chloride, or lithium chloride. The aqueous phase may further comprise, or be adjusted to comprise, a lower alcohol, such as isopropyl alcohol, methanol, ethanol, n-butanol, isobutanol or sec-butanol, or mixtures of two or more thereof.

Removing the organic solvent from the washed extract may comprise distillation, which may comprise heating to a temperature sufficiently high to remove any contaminating water, e.g., about 105° C. The distillation may also comprise recycling at least some of the organic solvent, e.g., by removing any contaminating water from the organic solvent before recycling the organic solvent to an earlier step. Step (g) may comprise applying a vacuum, heat, or agitation to the concentrated washed extract. The vacuum may be less than or equal to about 20 Torr, the temperature may be about 125° C., and/or agitation may be applied for at least two hours. The kinetics of decarboxylation may be accelerated, or lower temperatures may be used, e.g., by adding copper salts, limonene or vitamin B6. Decarboxylating the concentrated washed extract of step (g) may comprise applying a vacuum, heat, and agitation to the concentrated washed extract. Step (g) may also comprise an inert gas sweep, such as a nitrogen or argon sweep. The vacuum distillation may comprise wiped film distillation or similar short path distillation. The dewaxing step (i) may comprise dissolving the distillate in a solvent, adding a filter aid to the solvent, cooling the solvent, filtering, and collecting post-dewax filtrate. The solvent may be acetone, methanol or ethanol and the filter aid may comprise diatomaceous earth or similar filter aid, such as powdered cellulose (e.g., Solka Floc). The solvent may be recycled. The degassing of step (k) may comprise applying a vacuum, applying an inert gas sweep, applying heat, or agitation. The vacuum may be less than or equal to about 20 Torr, the applied heat may be sufficient for a temperature of about 125° C., the inert gas sweep may be a continuous nitrogen sweep, and/or the agitation may be applied for at least one hour. The vacuum distillation of step (l) may comprise wiped film distillation or similar short path distillation.

Also disclosed is a CBD concentrate manufactured by the method of the preceding paragraph.

BRIEF DESCRIPTION OF THE DRAWINGS

The following disclosure contemplates various systems and methods for refining cannabidiol (CBD) into one or both of a distillate or isolate.

DETAILED DESCRIPTION OF THE INVENTION

Figure 1:
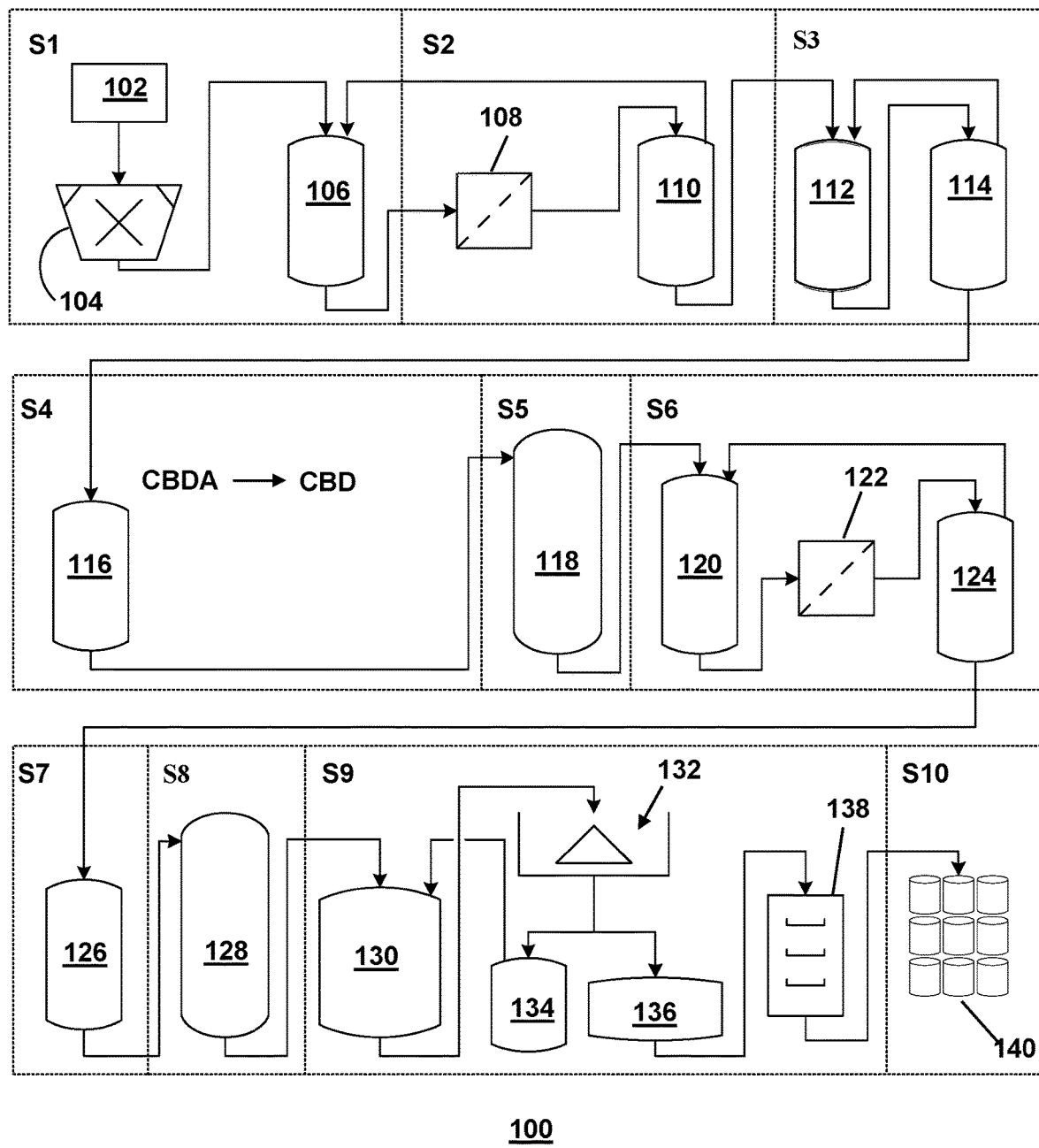
FIG. 1 depicts a block diagram outlining a method of manufacturing a cannabidiol (CBD) extract.

Various systems and methods for refining CBD are described herein and in the accompanying figures. Although described as including specific components, machinery and/or process steps, this is for illustrative purposes only as the disclosed embodiments are merely exemplary of the invention which can be embodied in various forms.

Therefore, specific structural and functional details disclosed herein are not to be interpreted as limiting, but merely as a representative basis for teaching one skilled in the art to variously employ the inventive arrangements utilizing any number of different components and method steps each capable of performing the described functionality.

As described herein, a process for refining CBD can include several different steps, which may be performed in the order described below or other orders. The steps can include one or more of the following:

- milling a raw material to produce a milled raw material,
- contacting the milled raw material with an extraction solvent to and separating a solid waste material from a raw extract,
- concentrating the raw extract to form a concentrated extract,
- washing the concentrated extract by dissolving the concentrated extract in an organic solvent to form an organic phase and washing the organic phase with an aqueous phase
- separating the aqueous phase from the organic phase to form a washed extract,
- removing the organic solvent from the washed extract to form a concentrated washed extract,
- decarboxylating the concentrated washed extract to form a post-decarboxylation extract,
- vacuum distilling the post-decarboxylation extract to form a distillate,
- dewaxing the distillate to form a post-dewax filtrate,
- applying a vacuum to the post-dewax filtrate to form a post-dewax concentrate,
- degassing the post-dewax concentrate to form a degassed concentrate,
- vacuum distilling the dewaxed concentrate to form a distilled CBD concentrate, and/or
- crystallizing CBD from the distilled CBD concentrate to form the CBD Isolate.

As used herein, the word "or" is inclusive, unless otherwise stated. Thus, "X or Y" logically includes, X, Y, or X and Y. Exclusive conjunction may be indicated by the phrase "either . . . or . . . ," or "one of . . . , or . . . ", or words to similar effect, e.g., "either X or Y" or "one of X, Y, or Z".

The terms "a" and "an" can refer to one of or a plurality of the elements they modify (e.g., "an organic solvent" can mean one or more organic solvents) unless it is contextually clear otherwise.

As used herein, the term "comprising" is means that the compositions or methods include the recited components or steps and do not exclude others. "Consisting essentially of" means that the claims are open only for the inclusion of components or steps that do not materially affect the basic and novel characteristics of the claimed compositions and methods. "Consisting of" excludes from the claim any step or component not specified in the claim. Embodiments defined by each of these transition terms are within the scope of this disclosure. Wherever the term "comprise" and its grammatical variants are used in this disclosure, the terms "consisting of" and "consisting essentially of" are implicitly disclosed as well, since the technology disclosed herein can be practiced in the absence of any components or steps not specifically disclosed herein. Thus, in accordance with the methods and compositions disclosed herein, in each instance herein any of the term "comprise" and its grammatical variants can be replaced with the terms "consisting essentially of," and "consisting of."

The term "about" as used herein refers to a value within 10% of the underlying parameter (i.e., plus or minus 10%). For example, a temperature of "about 100° C." can include temperatures between 90° C. and 110° C.

Reference is made herein to a "CBD extract." A "CBD extract" may, unless otherwise stated, comprise CBD, CBDA, or both.

Reference is made herein to "raw material." The "raw material" is any suitable material containing CBD, CBDA, or both. The methods described herein may be used to purify and isolate CBD from a raw material containing CBD, CBDA, or both. The CBD and CBDA may be present in the raw material in any proportion. As CBD, CBDA, or both will be carried throughout the process, unless otherwise stated, filtered extract, concentrated extract, organic phase, and concentrated washed extract may contain CBD, CBDA, or both, in any proportion.

In some embodiments, methods described herein result in high purity CBD Isolate. The high purity CBD Isolate may be crystalline. In some embodiments, the CBD Isolate may have a purity of greater than 98% (w/w). In some embodiments, the CBD Isolate may have a CBD purity of ≥98.5% (w/w), ≥98.6% (w/w), ≥98.7% (w/w), ≥98.8% (w/w), or ≥98.9% (w/w), e.g., about 98.5% (w/w) to about 99.0% (w/w), or about 99.0% (w/w) to about 98.95% (w/w), wherein the numerator represents weight of CBD in the CBD Isolate and the denominator represents the weight of the CBD Isolate. In some embodiments, CBD may be ≥98.5% (w/w), ≥98.6% (w/w), ≥98.7% (w/w), ≥98.8% (w/w), ≥98.9% (w/w), ≥99.0% (w/w), ≥99.1% (w/w), ≥99.2% (w/w), ≥99.3% (w/w), or ≥99.4% (w/w) of the total cannabinoids in the CBD Isolate. In some embodiments, the CBD Isolate contains ≤0.3% (w/w) THC. In some embodiments, the CBD Isolate contains ≤0.25% (w/w) THC, ≤0.2% (w/w) THC, ≤0.15% (w/w) THC, ≤0.1% (w/w) THC, ≤0.05% (w/w) THC, or ≤0.02% (w/w) THC, ≤0.01% (w/w) THC, or 0.0% (w/w) THC.

An advantage of the described methods is that they can use hemp in varying stages of decarboxylation of cannabinoids. Another advantage of the described methods is that they do not need, and in many cases, do not use chromatographic columns to effect separation of CBD or CBDA from a raw extract. Thus, in cases in which columns are avoided, the described methods can avoid the complications of chromatographic columns, including mobile phase mixing and flow control and waste associated with stationary phase cleaning and regeneration.

A process of isolating CBD will now be described with reference to FIG. 1, in which flow arrows indicate the transfer of materials, such as raw material, solvent, and extract, from one stage in the process to another. The arrows do not necessarily imply direct connections between one processing step and the next—there may be intermediate vessels between processing steps, where extract in various stages of processing may be collected and held for later processing. For example, where it is stated that a process step may be carried out in a batch fashion, it may be inferred that the arrows terminating at the process step include intermediate collection in vessels for holding a portion of the in-process extract prior to its being processed in the next step. Additionally, polishing filtration may be used between steps, wherein a liquid may be passed through a filter as it is transferred from one vessel to another to clarify or polish the liquid.

Raw Material

Turning to FIG. 1, a process 100 begins in step S1 with a raw material 102. The raw material 102 may be any plant material that contains cannabinoids, including cannabidiol (CBD), cannabidiolic acid (CBDA), tetrahydrocannabinol (THC), tetrahydrocannabinolic acid, cannabinol, cannabigerol, etc. The raw material 102 may contain CBD, CBDA, or both. The extraction process described herein is suitable for extracting both CBD and CBDA, in any relative proportions, from the raw material. The raw material may contain CBD and CBDA in various weight ratios, e.g., from about 10000:1 to about 1:10000, about 1000:1 to about 1:1000, about 100:1 to about 1:100, about 1:20 to about 20:1. Exemplary raw materials include hemp and various cultivars of *Cannabis sativa, Cannabis indica*, or *Cannabis ruderalis*. The raw material may be dried and/or subjected to analytical testing prior to milling. In some preferred embodiments, the raw material 102 comprises hemp.

Analytical Testing

Prior to milling, the raw material 102 may be subject to analytical testing, including identifying cannabinoids, determining their potency, and conducting related cannabinoid analysis of the raw material. A general class of analytical method that may be employed is a High Performance Liquid Chromatography (HPLC). An exemplary HPLC test method, HPLC Method I, described below, permits analysis of cannabidiol isolate for identification and potency of CBD and related cannabinoids.

HPLC Method I

The HPLC system parameters are listed in Tables 1 and the gradient conditions are listed in Table 2.

TABLE 1

HPLC System Parameters.

| | |
|---|---|
| Column Type: | Agilent Poroshell 120 EC-C18, 4.6 × 100 mm, 2.7 μm, PN 695975-902T |
| Guard Cartridge: | Phenomenex Security Guard Cartridge Holder, PN KJ0-4282 |
| Phenomenex Security Guard | C18, 4.0 × 3.0 mm, PN AJO-4287 |
| Column Temperature: | 35° C. |
| Sample Tray Temperature: | Ambient |
| Flow Rate: | 1.4 mL/min |
| Stop Time: | 12 minutes |
| Post Time: | 3 minutes |
| Method Type: | Gradient |
| MP A: | 0.015% Formic Acid in Water |
| MP B: | 0.010% Formic Acid in Acetonitrile |
| UV Detection | 240 nm |

TABLE 2

Gradient Conditions.

| | Gradient | |
|---|---|---|
| Time (min) | MPA (%) | MPB(%) |
| 0.0 | 30.0 | 70.0 |
| 2.0 | 30.0 | 70.0 |
| 8.0 | 5.0 | 95.0 |
| 12.0 | 5.0 | 95.0 |

Standard A Preparation using in-house standard or Crystalline Primary Standard Material: Weigh 100.0±10.0 mg of in-house cannabidiol isolate standard and quantitatively transfer into a 100.0 mL volumetric flask and add a sufficient volume of MeOH to bring the liquid level just below the QS line. Sonicate at Room Temperature (RT) for 2 minutes. Allow to equilibrate to room temperature then dilute to volume with MeOH and mix thoroughly. Dilute 5.0 mL of this solution to 50.0 mL with MeOH. This is the Standard A Preparation with a nominal concentration of 100 μg/mL cannabidiol.

Isolate Sample Preparation (Related Cannabinoids): Weigh 100.0±10.0 mg of finished product sample material and quantitatively transfer into a 100 mL volumetric flask and add a sufficient volume of MeOH to bring the liquid level just below the QS line. Sonicate at RT for 2 minutes. Allow to equilibrate to room temperature then dilute to volume with MeOH and mix thoroughly. This is the Related Cannabinoid Sample Preparation with a nominal concentration of 100 μg/mL.

Dilute 5.0 mL of the Related Compound Sample Preparation from Section to 50.0 mL using MeOH. This is the potency sample preparation with a nominal sample concentration of 100 μg/mL.

Milling

The raw material 102 may next be introduced into a mill 104 to increase the effective surface area of the raw material 102 and/or improve its handling characteristics. Milling may be carried out with suitable equipment, such as a hammermill. Other suitable milling equipment, processes, or process parameters may be employed. For example, liquid nitrogen may be used as a processing aid in the milling of hemp to render the raw material more brittle and thus more susceptible to the milling process. The milled raw material may be stored for future use or may be directly transferred to and extractor 106.

Extraction and Extraction Solvent

Extraction may be carried out in an extractor 106, in which milled raw material is contacted with a suitable extraction solvent. Suitable equipment may include a vessel of suitable size and resistance to chemicals used in the extraction process, such as stainless steel, glass, or glass-lined steel. Extraction solvent, such as a lower alcohol, e.g., methanol, ethanol, isopropyl alcohol, butanol (e.g., n-butanol), is charged to the extractor, after which milled raw material is added to the extractor 106. The contents of the extractor may then be agitated, e.g., at ambient temperature (e.g., about 15-30° C.). Extraction may be carried out in the cold, e.g. about 0° C. to about 15° C. to reduce co-extraction of waxes. After a period of about 1 minute to 30 minutes, the raw material solids may be separated from the extraction solvent, e.g., by transferring the extractor contents to a centrifuge and centrifuging at 3000 rpms. Extraction may be carried out in repeated stages, e.g., by two (or more) stages of counter-current extraction followed by separation of solids from the extraction solvent containing CBDA, CBD or both. After centrifugation, filtration, or preferably both, a supernatant containing CBDA, CBD, or both is separated from solids. A suitable centrifuge is a decanter centrifuge. The supernatant is a raw extract, which may be stored in a holding vessel or transferred directly to a further separation step to remove fine raw material particulates. The separated solids are waste material, which may be stored for further processing.

Separating Solid Waste Material from Raw Extract

Filtering and concentration are shown in step S2. The raw extract from the previous step may be filtered in a semi-continuous fashion to remove any residual fine raw material particulates from the extraction solvent. A portion of raw extract may be charged to a mixing vessel, followed by a filter aid, such as diatomaceous earth (DE). The raw extract and filter aid may be agitated together at ambient temperature. The contents of the vessel may then be transferred to a hydraulic filter press 108 or similar device. The filter of the filter press 108 may be precoated with a filter aid in a solvent (e.g., diatomaceous earth in IPA) prior to passing the contents of the vessel through the filter press 108. In an alternative embodiment, a filter media comprising a filtration aid (e.g., diatomaceous earth) impregnated in the filter media can be used. The filtrate, or process stream, may be recycled through the filter for a period of time, e.g., 20 min., under pressure, e.g., 20 psi, to pre-coat the filter. Following filtration, the filtrate may be transferred to an extract collection vessel. The filtrate may be further subjected to polishing filtration, e.g., by passing the filtrate through a 1 µm to 5 µm absolute filter prior to the next step. The process may be carried out in batches. Pressure may be adjusted to maintain a suitable flow rate, e.g., 20-80 psi and 1 gal/min. All filtrate (effluent), i.e., filtered extract, is transferred to the extract collection vessel, optionally after a polishing filtration step.

Concentrating Filtered Extract

The filtered extract may be concentrated by removing extraction solvent, e.g., by vacuum distillation in, e.g., a still 110. It may be desirable to leave some extraction solvent in the extract to maintain a desired consistency. For example, it may be desirable to leave up to 35% of isopropyl alcohol (IPA) in the extract. Concentrated extract may be stored while analysis is carried out. See HPLC Method I, above. Distillate (solvent) may be recycled to the extractor 106, e.g., after removing water from the solvent.

Washing Concentrated Extract

Washing and solvent recovery are depicted in step S3. Washing may begin by dissolving the concentrated extract in a suitable organic solvent, such as hexanes, heptanes, alkanes, benzene, xylenes, ethyl benzene, or toluene, or mixtures of two or more thereof. The washing step may be carried out in batches. The concentrate dissolved in organic solvent may first be charged to a suitable vessel, where it is then contacted with a suitable volume of an aqueous phase comprising water. The aqueous phase may comprise a suitable salt, such as magnesium sulfate or other suitable salt, such as sodium sulfate, potassium sulfate, lithium sulfate, sodium chloride, potassium chloride, or lithium chloride, or hydrates or combinations of any of the foregoing, as applicable. Together the organic solvent and extract form an organic phase. A suitable vessel 112 may be adapted to agitate the organic phase and aqueous phase, thereby increasing effective surface area and mass transfer between the two phases. After a suitable period of agitation, the aqueous phase and organic phase may be permitted to settle, with the denser aqueous phase containing polar contaminants removed from the extract settling on the bottom and the less dense organic phase containing CBD settling on top. (Halogenated solvents, such as carbon tetrachloride, trichloromethane, or methylene dichloride could also be used. Of course, if denser organic solvents, such as halogenated organic solvents, are used, the organic phase will be on the top.) The two phases may be separated, e.g., by drawing the aqueous phase from the bottom of the vessel 112 until all of the aqueous phase has been removed. After separation from the organic phase, aqueous phase may have residual organic solvent removed from it, e.g. by distillation so the water may be disposed in compliance with government regulations and the distillate may be disposed of, e.g., by off-site incineration. The separated organic phase constitutes a washed extract, which may then be transferred to a still 114 for concentration.

Concentration

The washed extract containing organic solvent from the washing step may be concentrated, e.g., by distillation in a still 114. Distillation may be carried out using suitable distillation equipment, which may be used to heat the washed extract. A suitable temperature for distillation may be, e.g., no more than 105° C. The organic solvent, e.g., hexanes, heptanes, alkanes, benzene, xylenes, ethyl benzene, or toluene, or mixtures of two or more thereof, may be collected, recovered, and recycled. The concentrated washed extract may then be transferred to a decarboxylation unit 116. About 0-3% (w/w) vegetable oil may be used to improve the viscosity of the concentrated washed extract for transfer to the decarboxylation step.

Decarboxylation

Decarboxylation is shown in step S4. Decarboxylation may comprise converting cannabidiolic acid (CBDA) to cannabidiol (CBD), as depicted in the following chemical reaction:

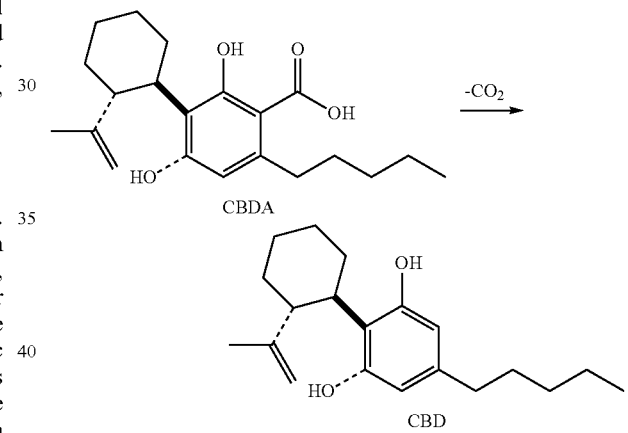

As can be seen, conversion of CBDA to CBD results in evolution of carbon dioxide ($CO_2$) gas, which may be removed by an inert gas stream and/or vacuum. Decarboxylation may be carried out in a batch fashion. Each batch may comprise, e.g., about 7 to 15 percent of the total mass of concentrated washed extract. Decarboxylation may be conducted under a vacuum of, e.g., ≤20 Torr, and may include an inert gas sweep. The inert gas sweep may comprise, e.g., nitrogen or some other inert gas capable of entraining carbon dioxide, such as argon. Decarboxylation may also function as a kill step to eradicate any pathogens present in the concentrated washed extract. Each batch may be heated to, e.g., 125° C., and may be agitated for a period of time sufficient to complete decarboxylation, e.g., at least two hours. The batch may then be cooled, e.g., to about 80° C., and transferred to a separate vessel. Vegetable oil, e.g., about 0-3% w/w (in some embodiments, about one liter), may be used to assist in transfer of the decarboxylated extract to the separate vessel.

Vacuum Distillation

Vacuum distillation, depicted in step S5, may be carried out in a vacuum distillation unit 118. The vacuum distillation unit 118 may be a molecular distillation unit, e.g., a wiped film evaporator or other type of short path evaporator. With a wiped film evaporator, it is possible to simultaneously separate lighter terpenes and sesquiterpenes from the cannabinoid distillates as these are evaporated away from the less volatile residue that remains in the residue. Vacuum distillation serves as a further purification step. Vacuum distillation may be performed in batch fashion using a suitable distillation unit 118, such as a wiped film distillation unit or similar short path distillation device. Each batch may comprise from about 7 to about 15 percent of the total decarboxylated extract. The decarboxylated extract may be fed into the distillation unit 118 at an elevated temperature, e.g., about 80° C. The extract may be distilled at a temperature of 170° C. to 200° C., e.g., approximately 185° C. (main column) under vacuum (e.g., about 300 mTorr or lower, such as about 150 mTorr to about 750 mTorr), using a using a high vacuum rotary vane oil sealed vacuum pump that may be paired with a turbomolecular or molecular diffusion pump and the distillate may be collected at a temperature in a range of about 60° C. to about 80° C., e.g., approximately 75° C. (internal condenser). The distillation step may comprise more than one pass through a distillation unit, e.g., a wiped film evaporator. On a first pass through a wiped film evaporator, low molecular weight terpenes may distill out of the extract with CBD. The terpenes may bypass the primary condenser to be captured in the "terp" trap at 0° C. to 5° C., or in the cold finger at ~-80° C., or in the vacuum oil of a molecular diffusion pump. As these lighter contaminants tend to result in higher pressures, after they are stripped out in earlier passes, later passes through the distillation unit can achieve improved vacuum and lower pressures. The distillate may be transferred to a separate vessel for dewaxing.

Dewaxing

Dewaxing of the distillate, depicted in step S6, begins with transfer to the distillate from the previous step into a dewaxing vessel 120. Dewaxing of the distillate may be performed in batch fashion. The distillate may be dissolved in a solvent, such as acetone, methanol or ethanol, or mixtures of two or more thereof, to form a solution. The proportion of solvent to distillate may be, e.g., about 2:1 to 3:1 (m/m). Each batch may comprise about 7 to about 17 percent of the total solution. After charging the solution to a suitable dewaxing vessel 120, a sufficient amount of a filter aid, such as diatomaceous earth or a similar filter aid, such as powdered cellulose (e.g., Solka Floc), may be added to the dewaxing vessel 120. The batch may then be cooled to a temperature of about −40° C. to −10° C., e.g., to ≤−20° C., under an inert gas atmosphere. Cooling may be achieved using liquid nitrogen gas in a heat exchanger through which the batch is recirculated. (An alternative method would be to blow liquid nitrogen through coils, onto which wax may collect.) The inert gas may be nitrogen or other suitable inert gas, such as argon. The batch may be agitated to mix the solution and filter aid. The batch may then be passed through a filter 122. The filter 122 may comprise a primary filter, which may be a filter cloth, which will catch the wax-filter aid agglomerate and allow the filtrate to pass through. A suitable filter is a Nutsche filter. The filtrate may be further filtered with a fine filter having a pore size of, e.g., 0.5 μm, at a suitable temperature of about −30° C. to about −10° C., e.g., at ≤−20° C., to remove additional fine solids. The fine filter may be a glass-wound submicron filter having a rating of about 0.5 μm. Upon completion of the filtration, the filter cake may be washed with cold solvent at a temperature in the range of about −30° C. to about 0° C., e.g., −20° C. acetone. The post-dewax filtrate may then be transferred to a concentration vessel for further processing.

Vacuum Concentration

Concentration of the post-dewax filtrate may comprise distillation in a suitable distillation unit 124 at a suitable temperature of about 60° C. to about 105° C., e.g., ≤90° C. until no more distillate is collected. Concentration may be carried out under vacuum. Initially, the temperature may be at the low end of the stated range; but as the solvent (e.g., acetone) is removed, the temperature must be raised above 65° C. so that the concentrate flows. The concentrate may be recirculated on a heat exchanger that has steam on it. As solvent (e.g., acetone) fraction goes down, the temperature should be increased. The resulting post-dewax concentrate may be transferred to a separate feed vessel for further processing. The distillate, e.g., acetone, may be recovered and recycled for use in the dewax process.

Degassing

The degassing of the post-dewax concentrate, depicted in step S7, may be carried out in a suitable reactor 126. Degassing may be performed in batch fashion to facilitate the removal of residual solvent, such as acetone from the post-dewax concentrate. The post-wash extract may first be charged to a reactor 126 from a feed vessel. The batch may then be placed under vacuum of about 15 to 50 Ton, e.g., ≤20 Torr) with a continuous inert gas (e.g., nitrogen or argon sweep of 0-10% (v/v/m) (wherein v/v/m or VVM is volume of gas per volume of batch per minute). The batch may then be heated to a temperature of, e.g., about 125° C., and may be agitated for about 0.5 h to about 2 h, e.g., for ≥1 h. The batch may then be cooled to a temperature of about 65° C. to about 85° C., e.g., 80° C., and the degassed concentrate may be transferred to a separate feed vessel for further processing. Vegetable oil (e.g., about 0-3% (w/w) about 1 L) may be used to assist in the transfer of material out of the reactor 126.

Vacuum Distillation (Cycle 2)

A second cycle of degassing, depicted in step S8, may be carried out in batch fashion in a suitable distillation unit 128, e.g., a wiped film distillation unit or similar short path distillation unit. The degassed concentrate may be fed into the distillation unit 128 at an elevated temperature of about 65° C. to 85° C., e.g., about 80° C. The extract may be distilled at a temperature of about 170° C. to about 200° C., e.g., 185° C. (main column) under vacuum a vacuum of about 100 to about 750 mTorr, (e.g., about 300 to about 600 mTorr), and the distillate may be collected at a suitable temperature in a range of about 65° C. to about 80° C., e.g., about 75° C. (internal condenser). The resulting second distillate may then be transferred to a separate vessel for further processing.

Crystallization and Isolation of CBD

A portion, or all, of the second distillate may be processed in a final crystallization step, as depicted in step S9, and the remainder may be retained for use in a different process. In a crystallization vessel 130, a suitable recrystallization solvent, such as pentane, may first be charged under an inert gas, e.g., nitrogen, atmosphere. A portion of the second distillate may then be charged to the crystallization vessel 130, e.g., with agitation, followed by another portion of the recrystallization solvent. The batch may first be adjusted to a suitable temperature, e.g., between 17° C. and 19° C. for pentane, under an inert gas, e.g., nitrogen (or argon) atmosphere, with agitation. CBD Isolate Seed (e.g., about 20 g/kg second distillate) may then be added to the crystallization vessel, and the batch may be gradually cooled, e.g., over several hours to a suitable temperature of about −15° C. to about −40° C., e.g., approximately −30° C. Recrystallization solvent, e.g., pentane, may be recycled, e.g. by first removing water in a still 134 and then returning the pentane to crystallization vessel 130.

The crystallized CBD may be isolated, e.g., by centrifugation in a centrifuge 132 at a temperature of about −15° C. to about −40° C., e.g., −30° C., e.g., at about 1,000-1,250×g. The recrystallization product may then be washed with pre-cooled pentane at −5° C. to −7° C. The resulting wet cake product may be de-lumped using a sieve 136 and/or dried in a drier 138, e.g., under vacuum. For example, the de-lumped CBD Isolate may be dried at a temperature of, e.g., ≥47° C. and under a vacuum of, e.g., ≥20 in Hg for, e.g., ≥2 h. The resulting dried CBD Isolate may be cooled and immediately packaged in saleable units 140, as depicted in step S10, or stored for later use.

Figure 2:
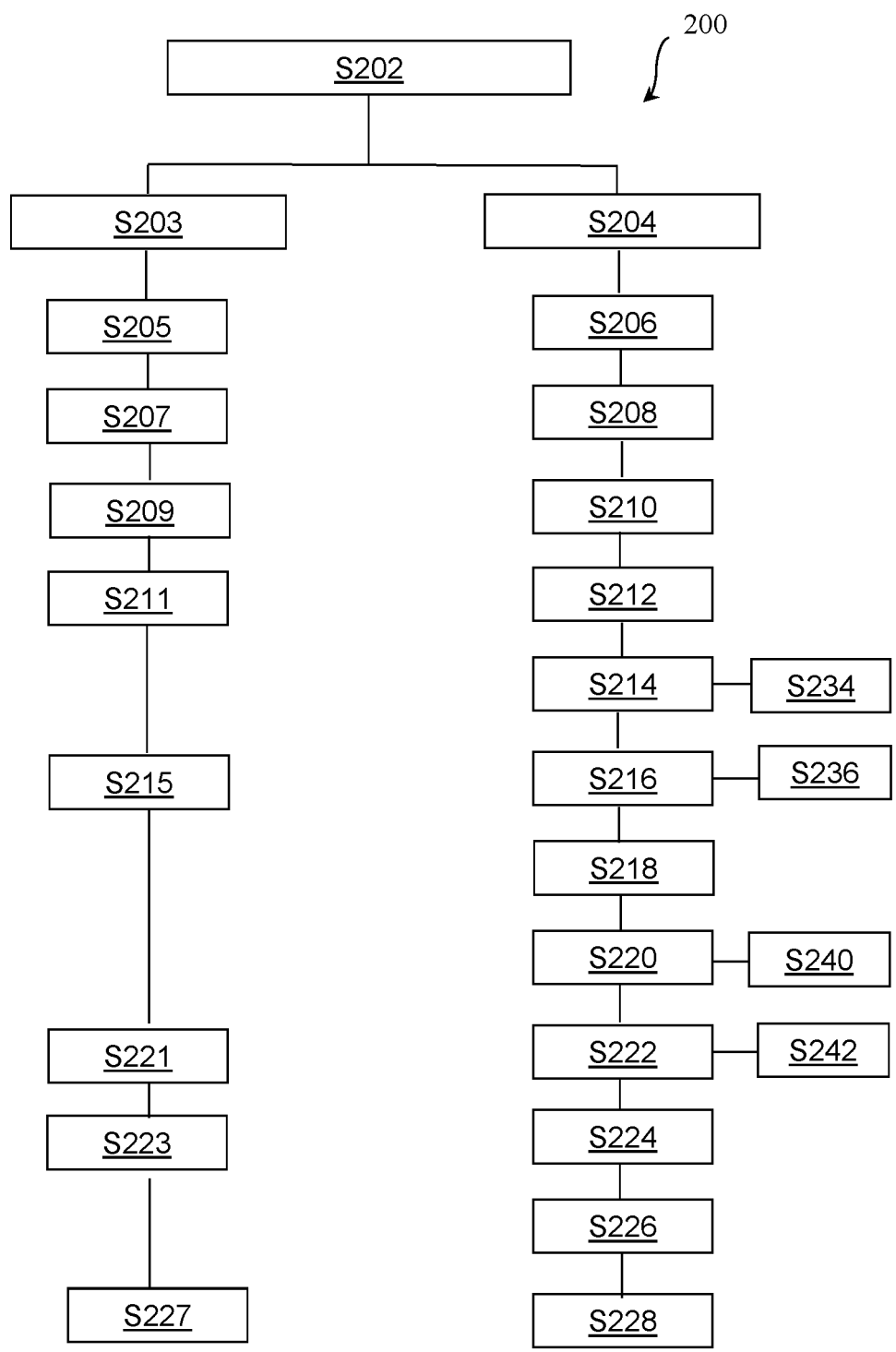
FIG. 2 depicts a flow diagram outlining a method of manufacturing a cannabidiol (CBD) extract.

FIG. 2 depicts a flow diagram of a process 200 for preparing a CBD Isolate from a cannabinoid-containing raw material, such as hemp. While reference is made to hemp as the starting material with reference to FIG. 2, one skilled in the art will recognize that other cannabis species and/or cultivars may be substituted for hemp. Step S202 represents pre-processing harvesting and drying of the hemp raw material.

The parallel vertical columns, topped by S203 on the left and S204 on the right, represent material flow (left) and process flow (right), respectively. In step S203, various processing aids, such as solvents and diatomaceous earth, as well as packaging, are received and subjected to quality control. In step S204, hemp raw material is received, sampled, and analyzed for cannabinoid identification and quantification. A suitable method of analysis is described in HPLC Method I, supra. Analysis may be carried out at several steps in the process to aid in maintaining in-process controls.

In step S205, trace numbers are assigned to received items, such as solvents, DE, and packaging materials, to aid in quality and inventory control. In step S206, hemp is tested, e.g., by HPLC Method I, and released for processing.

In step S207, processing aids and packaging are stored for later use. In step S208, the hemp raw material is milled to produce milled raw material hemp.

In step S209, an extraction solvent, e.g., isopropyl alcohol (IPA) or ethanol, is expended in the extraction step S210. The extraction step S210, described in more detail hereinabove, results in a raw extract. Hemp solid material may be discarded as waste.

In step S211, a filtration aid, such as diatomaceous earth (DE) or powdered cellulose (e.g., Solka Floc) is expended in the filtration step S212. Filtration step S211, described in more detail hereinabove, comprises mixing the DE with the raw extract and filtering, e.g., in a hydraulic filter press or centrifuge to remove fine particulate matter from the raw extract.

Processing on the right then passes to the evaporation step S214, which is described in more detail, above. Extraction solvent, e.g., a lower alcohol, such as methanol, IPA, ethanol (e.g., ethanol denatured with one or more alkanes), or a butanol (such as n-butanol), can be at least partially recovered from the filtrate of the previous step as a distillate in step S234.

After step S214, organic solvent, e.g., hexanes heptanes, alkanes, benzene, xylenes, ethyl benzene, or toluene, or mixtures of two or more thereof are expended in step S215 as organic solvent is charged into the wash step S216, which is described in more detail, above. Organic solvents may be at least partially recovered by evaporation in step S236.

After the wash step, the process on the right proceeds to a degas step S218, which is described in more detail, above. The degas step S218 is followed by a distillation step S220, which is described in more detail, above. Terpenes, sesquiterpenes, or both can be recovered in step S240.

After the distillation step S220, acetone is expended in step S221 as it is charged into the dewax step S222, which is described in more detail, above. The product of the dewax step is a post-dewax filtrate. Acetone can be recovered from the post-dewax filtrate by distillation in step S242 to form a post-dewax concentrate. In S220, acetone may be replaced by, or combined with, e.g., ethanol.

In step S223 on the left, pentane is expended as it is charged into recrystallization step S224, which is described in more detail, above. In step S226, the crystal CBD Isolate is sieved and dried in step S226, which is described in more detail, above.

In step S227, packaging is expended as the crystal CBD Isolate is packaged for distribution in step S228.

The following examples of CBD isolation processes are presented for illustrative purposes only and are not intended to be limiting.

Example 1

Acquiring the Raw Material

As described herein, the raw material (or host material) can include any number of different plants and other such materials containing cannabinoids, such as any amount of cannabidiol (CBD, CBDA, or both). In the preferred embodiment, the raw material can include, comprise or consist of Cannabis, Hemp or Marijuana (e.g., medical marijuana), for example; however, other plants, plant parts, or ingredients containing CBD, CBDA, or both (e.g., genetically modified yeast or yeast extract) are also contemplated.

The raw material can be dried using any number of known methodologies and/or equipment until the raw material reaches a specified moisture content. The raw material can be shipped and/or stored in any type of packaging and in any number of different amounts. The drying process can be performed upon receipt of the raw material at the processing facility or prior to receipt of the raw material. In one embodiment, the raw material can comprise medical marijuana (MMJ) that is shipped in fabric sacks containing about 140 kg of dried flowers, for example.

Milling the Received Raw Material

The milling step can function to reduce the size of the received and dried raw material to create more contact area for the extraction of CBD, CBDA, or both. In the preferred embodiment, a hammer mill can be used for this step; however, any number of other types of equipment capable of engaging the dried raw material and reducing the size of the same are also contemplated. As mentioned above, liquid nitrogen may be used as a milling aid to make the raw material more brittle and thus easier to mill.

In either instance, once the raw material has been reduced to a specified size, the milled material can be sifted to avoid clumping and can be stored in a moisture-controlled environment, such as a silo or other such location.

CBD/CBDA and Solid Material Separation

The next step in the process is to extract the CBD and CBDA from the milled material with an extraction solvent. Raw materials may contain varying proportions of acid (CBDA) to decarboxylate (CBD). In one preferred embodiment, this step can be performed via an ethanol extraction process that chemically pulls the CBDA and CBD from the milled material and centrifuges the non-extracted solids. During this step, a filter press or similar filter means can be utilized. The press can be prepared with activated carbon and diatomaceous earth to bind the filtered solids and prevent clogging of the equipment.

In another embodiment, a supercritical $CO_2$ extraction can be performed on the milled or non-milled raw material described above.

Of course, the inventive concepts are not to be construed as limiting to any particular extraction procedure, as any process capable of separating the CBD and CBDA from the solids contained within the raw material are also contemplated. To this end, any number of different machines and/or methodologies for performing this function may be utilized herein.

Evaporation Step

The evaporation step can function to remove a majority of the ethanol used in the proceeding step from the CBD extract. The CBD extract may contain CBD, CBDA, or both. The removed ethanol can be recovered and reused multiple times as additional processing occurs. This step may not be necessary when utilizing the above described supercritical $CO_2$ extraction. In either instance, this step can be run semi-continuously and can result in an oil material having approximately 75% CBD extract and 25% remaining ethanol.

As described herein, any number of different machines and processes capable of removing a specific amount of ethanol from the product are contemplated. By leaving some ethanol at the conclusion of this step, the method may advantageously promote the separation of the product into two distinct phases during the following step. This is important, because if a precise amount of alcohol is not left in the solution, the two phases will emulsify, thus rendering the final product unsuitable for its intended purpose.

Wash Step

In one embodiment, a 100 L portable tank, which is full of concentrated extract oil from the evaporation step, is moved to the washing area. The contents of the 100 L tank are transferred to the wash tank via nitrogen pressure. The wash tank has a capacity of 600 L, with a sight glass on the side, it is constructed of 316 SS. Once the concentrated oil extract has been transferred, hexane is added to the wash tank from hexane drums. Hexane is pumped into the wash vessel at a ratio of 1.57 L/kg of concentrated extract oil. In a normal batch, this is about 150 L. A flowmeter measures the volume of hexane. The hexane is added to act as a diluent to lower the density and dissolve the CBDA and CBD. Water is then added at a ratio of 1.93 L of water per kg of concentrated extract. In a normal batch, this is about 190 L.

The water is added to remove sugars, proteins, and some solid components. Then magnesium sulfate (or other salt, such as NaCl, KCl, or LiCl) is added to the top of the wash tank in a ratio of 10 g/kg of concentrated extract. In a normal batch, this is approximately 1.0 kg. The magnesium sulfate is added to help break emulsions and improve the separation of the two phases and impurities.

Once all the contents are added, the wash tank is agitated for a period of time, e.g., about 30 minutes. The mixture then settles for a period of time, e.g., about 1 hour to ensure adequate phase separation. The bottom phase, containing water, ethanol, and dissolved impurities, is then pressured out. This is where approximately two thirds of the remaining ethanol will exit the process. This phase is transferred to the collection tank located behind the wash tank. There is a sight glass at the wash tank outlet to detect when the phase break occurs. An operator will watch this and will shut off the valve when the rag layer starts to transfer to the collection tank. The wash tank outlet path will then be switched to the solvent recovery tank. The oil layer will then be pressure transferred over to the solvent recovery tank using Nitrogen.

Of course, the inventive methodology and process are not limited to these features, as any number of other materials, ratios and equipment can be utilized to perform the washing step.

Solvent Recovery Step

The recovery tank can include a 250 L capacity and can be constructed of 316 Stainless Steel. After all the contents are transferred, steam is applied to the jacket and the contents are agitated to improve heat transfer. The contents are held at 90° C. until solvent removal is complete. The hexane boils overhead and condensed in a plate and frame heat exchanger that is supplied cooling water. The rate of boiling is controlled by controlling the temperature of the distillate coming out of the condenser to less than 17° C. The condensed hexane is gravity fed into a recovered hexane drum. Some ethanol condenses with the hexane in the drum, but this is not a concern since the wash contains ethanol already. When operators note no additional hexane in the sight glass off the heat exchanger, the contents of the recovery tank are transferred to the pre-degas portable tank. The remaining washed CBD extract solution is about 70% CBD, CBDA, or both, with the remaining 30% being terpenes, other high boiling oils, and some waxes.

Of course, the inventive methodology and process are not limited to these features, as any number of other materials, ratios and equipment can be utilized to perform the solvent recovery step.

Decarb/Degas Step

The decarb/degas system can include a tank (referred to as "degas tank"), recirculation pump, heat exchanger, claw-style vacuum pump, pre-vacuum pump receiver, and post-vacuum pump muffler. The washed CBD extract can be transferred using nitrogen from the pre-degas portable 100 L tank to the degas tank. The degas tank has a capacity of 100 L with a bottom mounted agitator and is constructed of 316 SS.

Once CBD extract is transferred, the vacuum pump is opened and the pressure in the tank will begin to decrease. The recirculation pump is started, and the CBD oil is pumped around in a loop. Inside the top of the tank there is a spray ball that sprays the oil in the top of the tank. As an additional degassing device, nitrogen is bled into the top of the tank at the rate of about 60 SLH (~1 L/min.). The contents of the degas tank are heated to 125° C. and held there for about two hours. At this temperature and pressure many of the terpenes are above their boiling point. The boiled terpenes condense in the pre- and post-vacuum pump receivers, each with a 15 L capacity and constructed of 316 SS. During this heating period, the CBD undergoes decarboxylation.

Decarboxylation is the process of removing a carboxyl group, thus transforming the CBDA (the common, inactive form of CBD found in plants) into CBD. (Other cannabinoid acids, if present, may also be converted to the neutral form in the decarboxylation step.) About 13% (by weight) of the material converts to $CO_2$ and is offgassed. The second purpose of the degas/decarboxylation step is to remove low boiling compounds from the CBD oil so that a good vacuum can be obtained when the material is run through the wiped film evaporator.

After all contents have been decarboxylated, the remaining CBD oil is cooled by a double pipe heat exchanger in the recirculation piping. The heat exchanger uses 5° C. chilled water as the cooling source. The degas tank is then emptied via the lobe pump to a post-degas portable 100 L tank. Of course, the inventive methodology and process are not limited to these features, as any number of other materials, ratios and equipment can be utilized to perform the decarb/degas step.

Distillation Step

The distillation process can utilize a skid having a column (316 SS construction), three pumps (all gear pumps), and associated piping (lined 316 SS) as well as a vacuum pump, two heating units, a −85° C. chiller and a 5° C. chiller. The post-degas portable 100 L tank containing the CBD oil is connected to the skid in a recirculation loop. The feed pump on the skid transfers CBD oil from the bottom of the post-degas portable 100 L tank to the 9-inch wiped film evaporator (WFE) column at a rate of 20 kg/hr.

The liquid enters the top of the WFE and travels down past a wiper system. The column is operated under vacuum at an absolute pressure of 200-400 mTorr. The jacket of the evaporator is heated by hot Dynalene 600 at a temperature between 180° C. to 225° C. This is achieved with a commercial Mokon HTF-500 heater.

In the WFE column, when the liquid comes into contact with the hot walls, the CBD and any remaining terpenes are boiled. The boiled material enters an internal condenser in the middle of the column. This internal condenser uses 75° C. water/glycol, which condenses the CBD distillate. The cooling is provided by a commercial Mokon Hydrotherm II unit. The CBD then exits the bottom of the column and collects in a portable 20 L tank. This is the initial CBD distillate.

The internal condenser does not condense the remaining terpenes in the liquid. The terpenes exit the top of the column and are condensed in a heat exchanger that is supplied with 5° C. chilled water. The rate of condensing the terpenes is approximately 0.5 L/hr. The condensed terpenes range from gold to green in color and are collected in a 20 L tank constructed of 316 SS.

The remaining non-boiling material continues to the column bottom and is recirculated back to the post-degas portable 100 L tank to maximize CBD collection. Recirculation continues until condensed CBD distillate flow has stopped. The remainder of the material in the post-degas portable 100 L tank after removing the CBD and terpenes is black in color, considered waste, and contains waxes, sugars, and salts not previously removed from the extract. This material is dumped into the organic waste tote.

Uncondensed material is pulled toward the vacuum pump. Upstream of the vacuum pump is a cold trap, which is supplied a refrigerant from a chiller at −85° C. The cold trap captures any uncondensed terpenes before they can damage the vacuum pump. Periodically, the cold trap needs to be emptied. The condensed material contains terpenes, water, and other compounds which are dumped in the organic waste tote. Of course, the inventive methodology and process are not limited to these features, as any number of other materials, ratios and equipment can be utilized to perform the distillation step.

Dewax Step

The dewax tank is a jacketed, 316 SS vessel with a capacity of 250 L and a bottom mounted agitator. Acetone is added at a 3 kg/kg of CBD extract to the dewax tank via nitrogen pressure. In a normal batch, this is approximately 120 kg. The acetone is added at room temperature to help dissolve the CBD extract. CBD extract is poured from the multiple portable 20 L containers into the dewax tank until approximately 40 kg of material has been added. After the CBD extract has dissolved, the tank contents are cooled to −17° C. using a recirculating chiller with a liquid nitrogen booster heat exchanger. Once the liquid in the tank has reached −17° C., diatomaceous earth (DE) is poured into the dewax tank at a ratio of 100 g/kg of CBD extract with a maximum of 2.5 kg per batch (regardless of CBD extract amount). The contents in the dewax tank are then chilled to −20° C. This is an acceptable temperature for solidifying the wax.

It takes approximately two hours to reduce the temperature of the contents in the dewax tank to −20° C. After this temperature is reached, the solution is pressure transferred through a Buchner Filter. The average time to transfer all material through the filter is two hours. A 5 µm felt filter cloth is used in the Buchner Filter as the initial filtering media for the dewax tank contents. After the initial 10-15% of the material has been transferred, the DE/wax layer on the filter cloth become the filter media. The DE/wax layer may be washed with −20° C. acetone. The DE/wax layer is removed by hand after each batch. The DE/wax is waste. The solution is now dewaxed and is collected in a portable post-dewax 200 L stainless steel drum. Of course, the inventive methodology and process are not limited to these features, as any number of other materials, ratios and equipment can be utilized to perform the dewax step.

Solvent Recovery Step

The recovery tank has a 250 L capacity and is constructed of 316 SS. The post dewax drum contents are transferred using nitrogen. After all the contents are transferred, steam is applied to the jacket and the contents are agitated to improve heat transfer. The contents are held at 90° C. until solvent removal is complete. The acetone boils overhead and condensed in a plate and frame heat exchanger that is supplied 5° C. chilled water. The rate of boiling is controlled by controlling the temperature of the distillate coming out of the condenser to less than 17° C. The condensed acetone is gravity fed into a recovered acetone drum.

When operators note no additional acetone in the sight glass off the heat exchanger, the contents of the recovery tank are transferred to the post-dewax portable 100 L tank.

The remaining washed CBD extract solution is about 75 CBD, with the remaining 25% being terpenes and other high boiling oils. Of course, the inventive methodology and process are not limited to these features, as any number of other materials, ratios and equipment can be utilized to perform the solvent recovery step.

Degas Step

The decarb/degas system includes a tank (referred to as "degas tank"), recirculation pump, heat exchanger, claw-style vacuum pump, pre-vacuum pump receiver, and post-vacuum pump receiver. The dewaxed CBD extract is transferred using nitrogen from the post-dewax portable 100 L tank to the degas tank. The degas tank has a capacity of 100 L and is constructed of 316 SS. The degas tank has a capacity of 100 L with a bottom mounted agitator and is constructed of 316 SS.

Once CBD extract is transferred, the system is put under vacuum of less than 40 Torr. The contents of the dewax tank are heated to 125° C. and held there for up to two hours. Any residual acetone is pulled off the recirculating CBD oil. The remaining CBD oil is cooled by a shell and tube heat exchanger in the recirculation piping. The heat exchanger uses 5° C. chilled water as the cooling source. The degas tank is then emptied via the lobe pump to a post-degas portable 100 L tank. Of course, the inventive methodology and process are not limited to these features, as any number of other materials, ratios and equipment can be utilized to perform the degas step.

Second Distillation Step

The second distillation process is carried out in similarly to the first pass though the wiped film evaporator. However, in contrast to the first pass though the wiped film evaporator, the material is sent to crystallization rather than dewax.

Crystallization Step

The crystallization tank has a capacity of 200 liters, a top mounted mixer, and is constructed of 316 SS. Room temperature pentane, which helps dissolve the CBD extract, is pumped at a 3 L/kg CBD extract ratio to the crystallization tank via an air-operated double-diaphragm pump (AODD). An average crystallization batch consists of approximately 40 kg of CBD extract and 120 L pentane. The CBD extract is poured into the tank. The contents of the tank are cooled to approximately 15° C. Then 100 grams of CBD seed crystals are added to the tank. The seed crystals are used to promote the crystallization process. The crystal liquor is slowly cooled over two hours to a temperature of −20° C. The mixture is slowly stirred during this time at a speed of 50 rpm utilizing an anchor agitator.

After the solution has cooled to −20° C. the solution is pumped to a perforated bowl centrifuge by a progressive cavity pump. The mother liquid (ML) discharging from the centrifuge is collected into a 20 L 316 SS pot and then pumped by an AODD pump to the ML portable 200 L drum. ML will continue to discharge for approximately five minutes; operators visually ensure no ML is being discharged. Once ML has stopped discharging from the centrifuge, a cold pentane rinse is used to wash any residual ML off the CBD crystals. The wash process takes approximately five minutes; operators visually ensure the wash liquid is clear. The CBD crystals accumulate on the filtration back located along the wall of the centrifuge. The CBD crystals are removed by hand after each batch. The crystals are then sifted and sent over to the drying operation. Of course, the inventive methodology and process are not limited to these features, as any number of other materials, ratios and equipment can be utilized to perform the crystallization step.

Pentane Recovery Step

Mother Liquid is sucked into an evaporator using vacuum. The 50-liter rotary evaporator is submerged in a heating media under a slight vacuum. The rotary evaporator is heated to 50° C. The pentane evaporates from the ML and condenses on coils overhead. The liquid pentane gravity feeds into a glass collection drum. The collection drum is then pumped via an AODD back to a pentane storage drum. The concentrated ML is collected and stored in 5-gal pails for future processing. Of course, the inventive methodology and process are not limited to these features, as any number of other materials, ratios and equipment can be utilized to perform the pentane recovery step.

Drying Step

The CBD crystals are damp with pentane when they are removed from the basket centrifuge. The CBD crystals are sifted by hand and then evenly distributed into an 18-inch by 18-inch×1.5-inch SS pan. The SS pan is placed in the vacuum dryer. The vacuum dryer holds six trays. The CBD is dried using a vacuum of at least 20 in Hg and temperature of 121° F. for at least two hours. This reduces the pentane content of the CBD crystals to less than 500 ppm. Of course, the inventive methodology and process are not limited to these features, as any number of other materials, ratios and equipment can be utilized to dry the CBD crystals.

Packaging

After the CBD crystals are sufficiently dried, operators can use a scoop to add material to one 1-kg plastic containers. A container is placed on the calibrated scale and filled to 1 kg. The container lid is secured, and a cGMP-compliant label is added with batch number, gross tare weight, and warning information. Of course, any number of other packaging materials, sizes and information are also contemplated depending on the ultimate use or destination of the packaged product.

Example 2

Description of the Manufacturing Process

A brief description of the manufacturing process for a representative commercial batch size (approximately 100-250 kg) of CBD Isolate is provided in this example. In general, the manufacturing process can be divided into two main segments, the first being the preparation of crude hemp extract from raw hemp (Steps 1-2); the second segment entails conversion of crude hemp extract to CBD Isolate (Steps 3-10). The description is intended to summarize the key operations associated with the manufacture of CBD Isolate, and process parameters will vary based on batch size. The procedure described below includes in-process controls (IPCs), and typical mass yields are given at the end of each step.

Process yields may be determined by a suitable method. In the following tables, the analytical method of HPLC Method I, supra, is used to determine the concentration of cannabinoids in at each major process step. A summary of the overall process quantities and yield is presented in Table 1.

TABLE 1

Overall process quantities and yield:

|  | Starting Hemp (kg) | CBD Available in Hemp (kg) | Actual Isolate Yield (kg) | Contained CBD Isolate Yield (% w/w) |
|---|---|---|---|---|
| # of Lots | 111 | 111 | 111 | 111 |
| Minimum | 861.4 | 57.1 | 30.0 | 18% |
| Maximum | 7120.9 | 591.0 | 308.0 | 74% |
| Average | 3877.6 | 336.4 | 169.6 | 50% |
| Std. Dev | 1211.5 | 124.7 | 68.9 | 10% |

Step 1—Raw Hemp Milling and Extraction

Raw Hemp Milling

Each lot of raw hemp is initially subjected to analytical testing prior to release for use in production. A summary of the cannabinoid profile of incoming hemp is provided in Table 2.

TABLE 2

Cannabinoid profile of incoming hemp

|  | Hemp CBD | Hemp CBDA | Hemp THC | Hemp THCA | Total CBD | Total THC | CBD:THC Ratio |
|---|---|---|---|---|---|---|---|
| # Samples | 115 | 115 | 115 | 115 | 115 | 115 | 115 |
| Minimum (% w/w) | 0.00 | 0.07 | 0.00 | 0.06 | 0.06 | 0.05 | 0.91 |
| Maximum (% w/w) | 4.04 | 10.35 | 0.22 | 0.34 | 9.47 | 0.30 | 40.55 |
| Average (% w/w) | 0.81 | 6.47 | 0.06 | 0.18 | 6.49 | 0.22 | 29.31 |
| Std. Dev. (% w/w) | 0.86 | 2.51 | 0.07 | 0.07 | 2.54 | 0.08 | 7.27 |

In a representative operation cycle, a total of approximately 4585 kg of raw hemp is fed through a hammermill in portions, and the resulting milled hemp is either packaged into drums (approximately 100-110 kg each) or conveyed directly into the subsequent extraction step.

Extraction of the Milled Hemp

The extraction of the milled hemp is performed in portions in a semi-continuous fashion to provide a raw hemp extract. In a representative cycle, approximately 260-286 kg of isopropyl alcohol (IPA) (1.3 gal/kg milled hemp) is charged to an extractor. Approximately 200-220 kg of milled hemp is then added to the extractor containing the IPA, and the hemp extraction slurry is agitated at ambient temperature. The batch is transferred to a centrifuge for separation of the raw hemp extract from the extracted hemp solids at 3000 rpms. The raw hemp extract is stored in a separate holding tank for further processing, and the hemp waste solids are segregated for reclamation.

Step 2—Raw Hemp Extract Filtration and Concentration

Raw Hemp Extract Filtration

Filtration of the raw hemp extract is performed in portions in a semi-continuous fashion in order to remove fine raw hemp particulates remaining in the IPA process stream following the prior extraction/centrifugation sequence. In a representative cycle, a portion of approximately 50 gal of raw hemp extract is first charged to a mixing vessel. Approximately 2 kg of diatomaceous earth (DE) filter aid is then charged to the mixing vessel, and the contents are agitated at ambient temperature. The initial hemp extract slurry is transferred to a hydraulic filter press, and the process stream is recirculated through the press for 20 min at approximately 20 psi in order to pre-coat the filter. Following the initial filter pre-coat phase, the filtered extract is transferred to a collection vessel. Additional charges of raw hemp extract and DE (50 gal/1 kg) are performed in the mixing vessel, and the contents are filtered in portions through the filter press at 20-80 psi targeting a flow rate of 1 gal/min. All effluent from the filter press is combined into the filtered extract collection vessel.

Concentration of the Extract

Concentration of the filtered IPA extract is performed using vacuum distillation until a desired consistency is reached. The concentrated hemp extract may contain up to 35% IPA. Concentrated extract is drummed and sampled for assay analysis. The average expected mass yield for concentrated extract from raw hemp is approximately 21%. The IPA distillate may be recovered and recycled for use in the hemp extraction process. The cannabinoid profile of the concentrated extract (with all IPA removed) is summarized in Tables 3A and 3B.

TABLE 3A

Cannabinoid profile of concentrated extract.

|  | CBD | CBDA | CBDV | CBN | THC | THCA |
|---|---|---|---|---|---|---|
| # Samples | 14 | 14 | 14 | 14 | 14 | 14 |
| Minimum (% w/w) | 19.60 | 0.05 | 0.22 | 0.00 | 1.46 | 0.00 |
| Maximum (% w/w) | 57.70 | 37.62 | 0.35 | 0.20 | 2.37 | 0.51 |
| Average (% w/w) | 46.91 | 8.61 | 0.29 | 0.11 | 1.90 | 0.12 |
| Std. Dev. (% w/w) | 15.19 | 14.22 | 0.06 | 0.07 | 0.36 | 0.17 |

TABLE 3B

Cannabinoid profile of concentrated extract.

|  | Total CBD | Total THC | Other | Total RCs[1] | Total CNBDs[2] | Decarbed |
|---|---|---|---|---|---|---|
| # Samples | 14 | 14 | 14 | 14 | 14 | 14 |
| Minimum (% w/w) | 48.72 | 1.72 | 2.83 | 12.20 | 67.60 | 37.27 |
| Maximum (% w/w) | 57.74 | 2.47 | 10.04 | 59.97 | 79.57 | 99.92 |
| Average (% w/w) | 54.46 | 2.01 | 4.70 | 24.37 | 71.29 | 85.01 |
| Std. Dev. (% w/w) | 3.07 | 0.32 | 2.93 | 19.17 | 4.18 | 24.65 |

[1]RCs stands for related cannabinoids and includes cannabinoids other than CBD.
[2]CNBDs stands for "cannabinoids" and includes CBD plus RCs.

The average quantities for hemp extraction (steps 1-2) are summarized in Table 4.

TABLE 4

Step 1 and 2 (hemp extraction) process quantities and yield.

|  | Total milled hemp | Total concentrated extract | Mass Yield |
|---|---|---|---|
| # of Lots | 18 | 18 | 18 |
| Minimum (kg) | 3196 | 405 | 13% |
| Maximum (kg) | 26821 | 7895 | 31% |
| Average (kg) | 11306 | 2657 | 22% |
| Std. Dev. (kg) | 7336 | 1959 | 5% |

Step 3—Washing of Raw Hemp Extract Concentrate

Washing of the Extract

The washing of the raw hemp extract concentrate with water is the first step in the conversion of the crude extract to CBD Isolate, and the total input for this step (750-1000 kg) defines the batch size for the final CBD Isolate product. The washing step is performed in batch fashion and commences with the dissolution of the extract in hexanes. In a representative production cycle, a total of approximately 758.0 kg of raw hemp extract concentrate is processed in batches (70-95 kg each). In a representative individual wash batch, 94.4 kg of raw hemp extract concentrate is first charged to an extraction vessel. Approximately 148.2 L hexanes (1.57 L/kg extract) are charged followed by 182.2 L water (1.93 L/kg extract). Approximately 944 g magnesium sulfate (MgSO$_4$) (10 g/kg extract) is charged to the extraction vessel, and the batch is agitated at ambient temperature under air atmosphere for approximately 0.5 h. Agitation is stopped, and the mixture settled for approximately 1 h, after which the phase separation is confirmed. If the phase separation is unsuccessful, additional IPA (10% w/w based on extract) may be charged to the extraction vessel followed by agitation (0.5 h) and settling (1 h) in order to enable the separation. Once the separation is determined to be complete, the lower aqueous phase is removed for disposal. The organic phase is transferred to a concentration vessel.

Concentration of the Washed Extract

Concentration of the organic phase is performed using distillation at ≤90° C. until no more distillate is collected. Concentrated extract is transferred to a separate feed vessel for further processing. The hexanes distillate may be recovered and recycled for use in the hemp extract concentrate wash process. The average step quantities and yield for the wash are summarized in Table 5.

TABLE 5

Step 3 (wash) quantities and yield.

|  | Extract In | Washed Oil Out | Step Yield |
|---|---|---|---|
| # of Lots | 57 | 57 | 57 |
| Minimum (kg) | 198 | 103.4 | 47% |
| Maximum (kg) | 1390.6 | 770.2 | 73% |
| Average (kg) | 946.8 | 540.2 | 57% |
| Std. Dev (kg) | 198.5 | 113.6 | 6% |

A representative cannabinoid profile of the washed extract is presented in Tables 6A and 6B.

TABLE 6A

Cannabinoid profile of washed extract.

|  | CBD | CBDV | CBC | d9 THC | d8 THC |
|---|---|---|---|---|---|
| # Samples | 2 | 2 | 2 | 2 | 2 |
| Minimum (% w/w) | 49.69 | 0.21 | 3.07 | 1.28 | 0.52 |
| Maximum (% w/w) | 50.23 | 0.22 | 3.09 | 1.30 | 0.54 |
| Average (% w/w) | 49.96 | 0.22 | 3.08 | 1.29 | 0.53 |
| Std. Dev. (% w/w) | 0.38 | 0.00 | 0.01 | 0.01 | 0.02 |

TABLE 6B

Cannabinoid profile of washed extract.

|  | CBG | CBN | Total CNBDs[1] |
|---|---|---|---|
| # Samples | 2 | 2 | 2 |
| Minimum (% w/w) | 0.45 | 0.27 | 60.52 |
| Maximum (% w/w) | 0.45 | 0.28 | 60.56 |
| Average (% w/w) | 0.45 | 0.27 | 60.54 |
| Std. Dev. (% w/w) | 0.00 | 0.00 | 0.03 |

[1]CNBDs stands for "cannabinoids" and includes CBD plus RCs.

Step 4—Decarboxylation (Kill Step)

The decarboxylation of the post-wash extract is performed in batch fashion and converts acidic cannabinoids to the corresponding neutral species (e.g., CBDA to CBD). The decarboxylation stage also functions as a kill step with respect to the eradication of pathogens present that could compromise the safety of the final product. In a representative production cycle, a total of approximately 506.2 kg of post-wash extract is processed in portions (35-75 kg each). In a representative batch, the post-wash extract is first charged to a reactor from a feed vessel. Vegetable oil (~500 mL) may be used to assist in the transfer of material to the reactor. The batch is then placed under vacuum (<20 Torr) with a continuous nitrogen sweep (~600 cc/min). The batch is then heated to approximately 125° C. and is agitated for ≥2 h. The batch is cooled to approximately 80° C. and is then transferred to a separate feed vessel for further processing.

Vegetable oil (~1 L) may be used to assist in the transfer of material out of the reactor. The average step quantities and yield for the first degas and decarboxylation step are summarized in Table 7.

TABLE 7

Step 4 (degas/decarboxylation) quantities and yield.

|  | Washed Oil In | Decarboxylated Oil Out | Step Yield |
|---|---|---|---|
| # of Lots | 57 | 57 | 57 |
| Minimum (kg) | 103.4 | 108.2 | 83% |
| Maximum (kg) | 770.2 | 764.2 | 103% |
| Average (kg) | 540.2 | 529.1 | 96% |
| Std. Dev. (kg) | 113.6 | 114.3 | 3% |

A representative cannabinoid profile of the degassed/decarboxylated oil is presented in Tables 8A and 8B.

TABLE 8A

Cannabinoid profile of degassed/decarboxylated oil.

|  | CBD | CBDV | CBC | d9 THC | d8 THC |
|---|---|---|---|---|---|
| # Samples | 4 | 4 | 4 | 4 | 4 |
| Minimum (% w/w) | 48.58 | 0.22 | 2.83 | 1.22 | 0.51 |
| Maximum (% w/w) | 52.64 | 0.23 | 2.96 | 1.36 | 0.56 |
| Average (% w/w) | 50.19 | 0.22 | 2.89 | 1.27 | 0.53 |
| Std. Dev. (% w/w) | 1.87 | 0.00 | 0.06 | 0.06 | 0.02 |

TABLE 8B

Cannabinoid profile of degassed/decarboxylated oil.

|  | CBG | CBN | Total CNBDs[1] |
|---|---|---|---|
| # Samples | 4 | 4 | 4 |
| Minimum (% w/w) | 0.43 | 0.27 | 58.48 |
| Maximum (% w/w) | 0.48 | 0.29 | 63.57 |
| Average (% w/w) | 0.44 | 0.28 | 60.46 |
| Std. Dev. (% w/w) | 0.02 | 0.01 | 2.36 |

[1]CNBDs stands for "cannabinoids" and includes CBD plus RCs.

Step 5—Wiped Film Distillation (First Cycle)

The vacuum distillation of the post-decarboxylation extract is a purification step and is performed in batch fashion using a wiped film distillation unit. In a representative production cycle, a total of approximately 490.4 kg of post-decarboxylation extract is processed in portions (37-72 kg each) to yield a total of approximately 314.0 kg of distillate. The post-decarboxylation extract is fed into the distillation unit at approximately 80° C. from the feed vessel. The extract is distilled at approximately 185° C. (main column) under vacuum (300-600 mTorr), and the distillate is collected at approximately 75° C. (internal condenser). The product distillate is transferred to a separate vessel for further processing. The average step quantities and yield for the first cycle distillation are summarized in Table 9.

TABLE 9

Step 5 (first cycle distillation) quantities and yield.

|  | Decarboxylated Oil In | 1st Cycle Distillate Out | Step Yield |
|---|---|---|---|
| # of Lots | 57 | 57 | 57 |
| Minimum (% w/w) | 108.2 | 60 | 49% |
| Maximum (% w/w) | 764.2 | 484.6 | 68% |
| Average (% w/w) | 529.1 | 318.1 | 60% |
| Std. Dev. (% w/w) | 114.3 | 70.7 | 5% |

A representative cannabinoid profile of the first cycle distillate is presented in Tables 10A and 10B.

TABLE 10A

Cannabinoid profile of first cycle distillate.

|  | CBD | CBDV | CBC | d9 THC | d8 THC |
|---|---|---|---|---|---|
| # Samples | 10 | 10 | 10 | 10 | 10 |
| Minimum (% w/w) | 72.95 | 0.31 | 3.94 | 1.58 | 0.71 |
| Maximum (% w/w) | 80.26 | 0.38 | 4.48 | 2.19 | 0.83 |
| Average (% w/w) | 77.95 | 0.35 | 4.30 | 1.83 | 0.78 |
| Std. Dev. (% w/w) | 2.19 | 0.02 | 0.16 | 0.18 | 0.04 |

TABLE 10B

Cannabinoid profile of first cycle distillate.

|  | CBG | CBN | Total CNBDs[1] |
|---|---|---|---|
| # Samples | 10 | 10 | 10 |
| Minimum (% w/w) | 0.45 | 0.26 | 87.40 |
| Maximum (% w/w) | 0.77 | 0.39 | 96.42 |
| Average (% w/w) | 0.58 | 0.32 | 93.16 |
| Std. Dev. (% w/w) | 0.09 | 0.04 | 2.84 |

[1]CNBDs stands for "cannabinoids" and includes CBD plus RCs.

Step 6—Dewaxing

Precipitation of the Wax and Filtration

The dewaxing of the distillate from the first distillation cycle is a purification step and is performed in batch fashion and commences with the dissolution of the distillate in acetone. In a representative production cycle, a total of approximately 313.8 kg of distillate is processed in portions (37-50 kg each). In a representative batch, approximately 80.0-120.0 kg acetone (2-3 kg/kg distillate) is first charged to a precipitation vessel from a feed vessel. Approximately 37.6 kg of distillate is then charged to the precipitation vessel with agitation followed by 1.5 kg of diatomaceous earth (DE) filter aid. The batch is first cooled to ≤−20° C. under nitrogen atmosphere with agitation. The batch is then filtered (0.5 μm) at ≤−20° C. to remove the solids. Upon completion of the filtration, the filter cake may be washed with cold (e.g., −20° C.) acetone. The post-dewax filtrate is transferred to a concentration vessel for further processing. The average step quantities and yield for the dewax are summarized in Table 11. Note that dewaxed distillate may contain residual acetone, affecting the calculated step yield.

TABLE 11

Step 6 (dewax) quantities and yield.

|  | Distillate In | Dewaxed Distillate Out | Step Yield |
|---|---|---|---|
| # of Lots | 57 | 57 | 57 |
| Minimum (kg) | 60 | 64.4 | 94% |
| Maximum (kg) | 484.6 | 510.4 | 119% |
| Average (kg) | 318.1 | 337.5 | 106% |
| Std. Dev. (kg) | 70.7 | 75.0 | 5% |

A representative cannabinoid profile of the dewaxed distillate is presented in Tables 12A and 12 B.

TABLE 12A

Cannabinoid profile of dewaxed distillate.

|  | CBD | CBDV | CBC | d9 THC | d8 THC |
|---|---|---|---|---|---|
| # Samples | 2 | 2 | 2 | 2 | 2 |
| Minimum (% w/w) | 69.26 | 0.31 | 3.81 | 1.60 | 0.71 |
| Maximum (% w/w) | 70.01 | 0.31 | 3.88 | 1.61 | 0.72 |
| Average (% w/w) | 69.64 | 0.31 | 3.85 | 1.61 | 0.72 |
| Std. Dev. (% w/w) | 0.53 | 0.00 | 0.05 | 0.00 | 0.01 |

TABLE 12B

Cannabinoid profile of dewaxed distillate.

|  | CBG | CBN | Total CNBDs[1] |
|---|---|---|---|
| # Samples | 2 | 2 | 2 |
| Minimum (% w/w) | 0.47 | 0.28 | 80.14 |
| Maximum (% w/w) | 0.50 | 0.29 | 81.59 |
| Average (% w/w) | 0.49 | 0.29 | 80.86 |
| Std. Dev. (% w/w) | 0.02 | 0.01 | 1.03 |

[1]CNBDs stands for "cannabinoids" and includes CBD plus RCs.

Concentration of the Filtrate

Concentration of the acetone filtrate is performed using distillation at ≤90° C. until no more distillate is collected. The concentrated dewax filtrate is transferred to a separate feed vessel for further processing. The acetone distillate may be recovered and recycled for use in the dewax process.

Step 7—Degassing

The degassing of the post-dewax concentrate is performed in batch fashion and facilitates the removal of residual acetone from the concentrate. In a representative production cycle, a total of approximately 333.4 kg of post-dewax concentrate is processed in portions (38-55 kg each). In a representative batch, the post-wash extract is first charged to a reactor from a feed vessel. Vegetable oil (~500 mL) may be used to assist in the transfer of material to the reactor. The batch is then placed under vacuum (≤20 Torr) with a continuous nitrogen sweep (~600 cc/min). The batch is then heated to 125° C. and is agitated for ≥1 h. The batch is cooled to 80° C., and the product is transferred to a separate feed vessel for further processing. Vegetable oil (~1 L) may be used to assist in the transfer of material out of the reactor. The average step quantities and yield for the second degas are summarized in Table 13.

TABLE 13

Step 7 (degas) quantities and yield.

|  | Dewaxed Distillate In | Degassed Oil Out | Step Yield |
|---|---|---|---|
| # of Lots | 57 | 57 | 57 |
| Minimum (kg) | 64.4 | 54.4 | 79% |
| Maximum (kg) | 510.4 | 473.3 | 96% |
| Average (kg) | 337.5 | 312.2 | 90% |
| Std. Dev. (kg) | 75.0 | 69.6 | 4% |

A representative cannabinoid profile of the degassed dewaxed distillate is presented in Tables 14A and 14B.

TABLE 14

Cannabinoid profile of degassed dewaxed distillate.

|  | CBD | CBDV | CBC | d9 THC | d8 THC |
|---|---|---|---|---|---|
| # Samples | 2 | 2 | 2 | 2 | 2 |
| Minimum (kg) | 73.21 | 0.33 | 3.96 | 1.67 | 0.73 |
| Maximum (kg) | 75.57 | 0.33 | 4.14 | 1.84 | 0.75 |
| Average (kg) | 74.39 | 0.33 | 4.05 | 1.76 | 0.74 |
| Std. Dev. (kg) | 1.67 | 0.00 | 0.12 | 0.12 | 0.01 |

TABLE 14B

Cannabinoid profile of degassed dewaxed distillate.

|  | CBG (% w/w) | CBN (% w/w) | Total CNBDs[1] (% w/w) |
|---|---|---|---|
| # Samples | 2 | 2 | 2 |
| Minimum | 0.50 | 0.29 | 86.27 |
| Maximum | 0.54 | 0.33 | 87.46 |
| Average | 0.52 | 0.31 | 86.86 |
| Std. Dev. | 0.03 | 0.03 | 0.84 |

[1]CNBDs stands for "cannabinoids" and includes CBD plus RCs.

Step 8—Wiped Film Distillation (Second Cycle)

The vacuum distillation of the product from the degassing step is the final purification in the process prior to the crystallization of the CBD Isolate and is performed in batch fashion using a wiped film distillation unit. In a representative production cycle, a total of approximately 313.0 kg of post-degassing product is processed in portions (36-55 kg each) to yield a total of approximately 283.9 kg of distillate. The post-degassing product is fed into the distillation unit at 80° C. from the feed vessel. The extract is distilled at 185° C. (main column) under vacuum (300-600 mTorr), and the distillate is collected at 75° C. (internal condenser). The product distillate is transferred to a separate vessel for further processing.

The average step quantities and yield for the second cycle distillation are summarized in Table 15.

TABLE 1

Step 8 (second cycle distillation) quantities and yield.

|  | Degassed Oil In | 2nd Cycle Distillate Out | Step Yield |
| --- | --- | --- | --- |
| # of Lots | 57 | 57 | 57 |
| Minimum (kg) | 54.4 | 50 | 86% |
| Maximum (kg) | 473.3 | 445.2 | 97% |
| Average (kg) | 312.2 | 288.8 | 92% |
| Std. Dev. (kg) | 69.6 | 65.9 | 2% |

The cannabinoid profile of the second cycle distillate is summarized in Tables 16A and 16B.

TABLE 16A

Cannabinoid profile of second cycle distillate.

|  | CBD | CBDV | CBDA | CBG | CBN | THC | THCA |
| --- | --- | --- | --- | --- | --- | --- | --- |
| # Samples | 177 | 176 | 176 | 95 | 176 | 176 | 176 |
| Minimum (% w/w) | 71.90 | 0.00 | 0.00 | 0.23 | 0.00 | 0.02 | 0.00 |
| Maximum (% w/w) | 85.40 | 0.69 | 0.69 | 1.79 | 0.63 | 4.14 | 0.02 |
| Average (% w/w) | 81.11 | 0.37 | 0.04 | 0.68 | 0.23 | 2.37 | 0.00 |
| Std. Dev. (% w/w) | 1.95 | 0.09 | 0.14 | 0.28 | 0.11 | 0.55 | 0.00 |

TABLE 16B

Cannabinoid profile of second cycle distillate.

|  | Total THC | THCV | Other | Total RCs[1] | Total CNBDs[2] |
| --- | --- | --- | --- | --- | --- |
| # Samples | 176 | 34 | 176 | 175 | 177 |
| Minimum (% w/w) | 0.02 | 0.00 | 0.04 | 10.28 | 76.50 |
| Maximum (% w/w) | 4.14 | 0.22 | 11.32 | 22.56 | 103.85 |
| Average (% w/w) | 2.37 | 0.10 | 3.60 | 14.02 | 94.96 |
| Std. Dev. (% w/w) | 0.55 | 0.07 | 1.69 | 2.82 | 3.32 |

[1]RCs stands for related cannabinoids and includes cannabinoids other than CBD.
[2]CNBDs stands for "cannabinoids" and includes CBD plus RCs.

Step 9—Final Crystallization and Isolation

Crystallization of CBD Isolate

The crystallization of CBD from the product of the second distillation cycle is the final purification step in the CBD Isolate manufacturing process. The crystallization is a seeded crystallization that employs a temperature ramp and is performed in batch fashion. The process commences with the dissolution of the distillate in pentane.

In a typical production cycle, a portion of the second distillate is processed in the final crystallization, and the remainder is retained for use in a different process. In a representative production cycle, a total of approximately 186.5 kg of distillate is processed in portions (26-45 kg each) to yield a total of approximately 97.7 kg of CBD Isolate. In a representative batch, approximately 72 kg pentane is first charged to a crystallization vessel under nitrogen atmosphere. Approximately 38.0 kg of distillate is then charged to the crystallization vessel with agitation followed by approximately 8 kg of pentane (80 kg total, 2 kg/kg distillate) to complete the transfer. The batch is first adjusted to approximately 17° C. under nitrogen atmosphere with agitation. CBD Isolate Seed (20 g/kg distillate) is charged to the crystallization vessel, and the batch is slowly cooled over approximately 3 h to approximately −30° C.

The crystallization product is isolated by centrifugation at −30° C. and is then washed with pre-cooled pentane at ≤−10° C. The wet cake product is first de-lumped using a sieve and is then dried under vacuum at ≥47° C. and ≥20 in Hg for ≥2 h.

The average step quantities and yield for the crystallization are summarized in Table 17.

TABLE 17

Step 9 (crystallization) quantities and yield.

|  | 2nd Cycle Distillate In | Isolate Out | Step Yield |
| --- | --- | --- | --- |
| # of Lots | 57 | 57 | 57 |
| Minimum (kg) | 50 | 34 | 63% |
| Maximum (kg) | 445.2 | 308 | 81% |
| Average (kg) | 288.8 | 199.4 | 71% |
| Std. Dev. (kg) | 65.9 | 51.1 | 4% |

The cannabinoid profile of the cannabidiol isolate is summarized in Tables 18A and 18B.

TABLE 18A

Cannabinoid profile of cannabidiol (CBD) Isolate.

|  | CBD | CBDV | CBDA | CBG | CBN | THC | THCA |
|---|---|---|---|---|---|---|---|
| # Samples | 1416 | 1415 | 1415 | 818 | 1415 | 1415 | 1415 |
| Average (% w/w) | 98.94 | 0.28 | 0.00 | 0.00 | 0.00 | 0.00 | 0.00 |
| Std. Dev. (% w/w) | 0.83 | 0.08 | 0.00 | 0.00 | 0.00 | 0.01 | 0.01 |

TABLE 18B

Cannabinoid profile of cannabidiol (CBD) Isolate.

|  | Total THC | THCV | Other | Total RCs[1] | Total CNBDs[2] |
|---|---|---|---|---|---|
| # Samples | 1412 | 367 | 1415 | 1415 | 1416 |
| Average (% w/w) | 0.00 | 0.00 | 0.23 | 0.53 | 99.47 |
| Std. Dev. (% w/w) | 0.01 | 0.00 | 0.02 | 0.08 | 0.82 |

[1]RCs stands for related cannabinoids and includes cannabinoids other than CBD.
[2]CNBDs stands for "cannabinoids" and includes CBD plus RCs.

Step 10—Packaging

The final CBD Isolate is packaged into double-lined (LDPE) aluminum containers. The container closure details are provided in Container Closure System section.

While the invention has been described with reference to certain illustrative embodiments, those described herein are not intended to be construed in a limiting sense. For example, variations or combinations of steps or materials in the embodiments shown and described may be used in particular cases without departure from the invention. Various modifications and combinations of the illustrative embodiments as well as other advantages and embodiments of the invention will be apparent to persons skilled in the arts upon reference to the drawings, description, and claims.

What is claimed is:

1. A method of manufacturing a CBD Isolate, comprising:
   (a) milling a raw material to produce a milled raw material;
   (b) contacting the milled raw material with an extraction solvent to form a raw extract and separating a solid waste material from the raw extract to form a filtered extract;
   (c) concentrating the filtered extract to form a concentrated extract;
   (d) washing the concentrated extract by dissolving the concentrated extract in an organic solvent to form an organic phase and washing the organic phase with an aqueous phase;
   (e) separating the aqueous phase from the organic phase to form a washed extract;
   (f) removing the organic solvent from the washed extract to form a concentrated washed extract;
   (g) decarboxylating the concentrated washed extract to form a decarboxylated extract;
   (h) vacuum distilling the decarboxylated extract to form a distillate;
   (i) dewaxing the distillate to form a post-dewax filtrate;
   (j) applying a vacuum to the post-dewax filtrate to form a post-dewax concentrate;
   (k) degassing the post-dewax concentrate to form a degassed concentrate;
   (l) vacuum distilling the degassed concentrate to form a distilled CBD concentrate; and
   (m) crystallizing CBD from the distilled CBD concentrate to form the CBD Isolate.

2. The method of claim 1, wherein the raw material is hemp.

3. The method of claim 1, wherein the extraction solvent comprises at least one of isopropyl alcohol, methanol, ethanol, n-butanol, isobutanol, or sec-butanol.

4. The method of claim 1, wherein the concentrating the filtered extract to form a concentrated extract comprises subjecting the raw extract to vacuum distillation.

5. The method of claim 1, wherein the organic solvent of step (d) comprises hexanes.

6. The method of claim 1, wherein the aqueous phase of step (d) comprises magnesium sulfate.

7. The method of claim 1, wherein the removing the organic solvent from the washed extract comprises distillation.

8. The method of claim 1, wherein the decarboxylating the concentrated washed extract of step (g) comprises at least one of applying a vacuum, applying heat, or agitation to the concentrated washed extract.

9. The method of claim 1, wherein the vacuum distillation comprises wiped film distillation.

10. The method of claim 9, wherein the aqueous phase further comprises, or is adjusted to comprise, isopropyl alcohol.

11. The method of claim 1, wherein the dewaxing step (i) comprises dissolving the distillate in a solvent, adding a filter aid to the solvent, cooling the solvent, filtering, and collecting a post-dewax filtrate.

12. The method of claim 11, wherein the solvent is acetone and the filter aid comprises diatomaceous earth.

13. The method of claim 1, wherein the degassing of step (k) comprises at least one of applying a vacuum, applying an inert gas sweep, applying heat, or agitation.

14. The method of claim 1, wherein the vacuum distillation of step (l) comprises wiped film distillation.

15. The method of claim 1, wherein the crystallizing the CBD Isolate comprises dissolving the distilled CBD concentrate of step (l) in a crystallization solvent at a first temperature; lowering the temperature to a second temperature lower than the first temperature; adding a crystal seed; lowering the temperature to a third temperature lower than the second temperature; and separating crystalized CBD to form the CBD Isolate.

16. A method of manufacturing CBD concentrate, comprising:
   (a) milling a raw material to produce a milled raw material;
   (b) contacting the milled raw material with an extraction solvent and separating a solid waste material from a raw extract;
   (c) concentrating the raw extract to form a concentrated extract;
   (d) washing the concentrated extract by dissolving the concentrated extract in organic solvent to form an organic phase and washing the organic phase with an aqueous phase;

(e) separating the aqueous phase from the organic phase to form a washed extract;
removing organic solvent from the washed extract to form a concentrated washed extract;
(g) applying a vacuum to the concentrated washed extract to form a post-decarboxylation extract;
(h) vacuum distilling the post-decarboxylation extract to form a distillate;
dewaxing the distillate to form a post-dewax filtrate;
applying a vacuum to the post-dewax filtrate to form a post-dewax concentrate;
(k) degassing the post-dewax concentrate to form a degassed concentrate;
(l) vacuum distilling the degassed concentrate to form a CBD concentrate.

17. The method of claim 16, wherein the raw material is hemp.

18. The method of claim 16, wherein the organic solvent of step (d) comprises hexanes and the aqueous phase comprises water and magnesium sulfate.

* * * * *

UNITED STATES PATENT AND TRADEMARK OFFICE
CERTIFICATE OF CORRECTION

PATENT NO. : 11,401,226 B2
APPLICATION NO. : 16/875744
DATED : August 2, 2022
INVENTOR(S) : Brad William Stone, Stephen Culhane Mueller and Casey James Kikendall It is certified that error appears in the above-identified patent and that said Letters Patent is hereby corrected as shown below:

In the Claims

Claim 10 should be amended as follows:
10. The method of claim 6, wherein the aqueous phase further comprises, or is adjusted to comprise, isopropyl alcohol.

Signed and Sealed this
Eleventh Day of October, 2022

Katherine Kelly Vidal
Director of the United States Patent and Trademark Office